United States Patent [19]

Turkel et al.

[11] Patent Number: 5,634,924
[45] Date of Patent: Jun. 3, 1997

[54] BIPOLAR ROLLER ELECTRODES AND ELECTROCAUTERY PROBES FOR USE WITH A RESECTOSCOPE

[75] Inventors: David Turkel; Kevin F. Hahnen, both of Miami, Fla.

[73] Assignee: Symbiosis Corporation, Miami, Fla.

[21] Appl. No.: 520,102

[22] Filed: Aug. 28, 1995

[51] Int. Cl.$^6$ .................................................. A61B 17/39
[52] U.S. Cl. ............................... 606/46; 606/41; 606/45; 606/49
[58] Field of Search .......................... 606/40, 41, 46–49

[56] References Cited

U.S. PATENT DOCUMENTS

| | | | |
|---|---|---|---|
| 2,484,059 | 10/1949 | Wallace | 128/303.15 |
| 3,920,021 | 11/1975 | Hiltebrandt | 128/303.17 |
| 4,060,087 | 11/1977 | Hiltebrandt et al. | 128/303.15 |
| 4,116,198 | 9/1978 | Roos | 128/303.15 |
| 4,674,498 | 6/1987 | Stasz | 128/303.14 |
| 5,078,717 | 1/1992 | Parins et al. | 606/48 |
| 5,080,060 | 1/1992 | Buelna | 606/45 |
| 5,395,363 | 3/1995 | Billings et al. | 606/48 X |

FOREIGN PATENT DOCUMENTS 8103271  11/1981  WIPO .................................. 606/46

Primary Examiner—Angela D. Sykes
Assistant Examiner—Stephen Huang
Attorney, Agent, or Firm—David P. Gordon

[57] ABSTRACT

A bipolar roller electrode has a non-conductive base upon which two electrical conductors are placed with a gap between the conductors. The electrode is provided with a blind hole at each end thereof for rotatably mounting it between a pair of arms. Each of the two conductors preferably extends into or forms a part of a respective blind hole. An electrocautery probe according to the invention includes a pair of electrically conductive arms between which the electrode is mounted with each of the arms entering one of the blind holes in the electrode. The arms are mechanically joined but electrically isolated and their proximal ends are individually coupled to a pair of electrode leads. A non-conductive or insulated mounting sleeve is preferably provided intermediate of the arms and the leads for slideably coupling the probe to a resectoscope. The distal end of each arm of the probe enters a respective blind hole in the roller electrode and makes electrical contact with a respective one of the two conductors. Several methods of manufacturing the electrodes are disclosed as are several different embodiments of the electrodes.

9 Claims, 4 Drawing Sheets

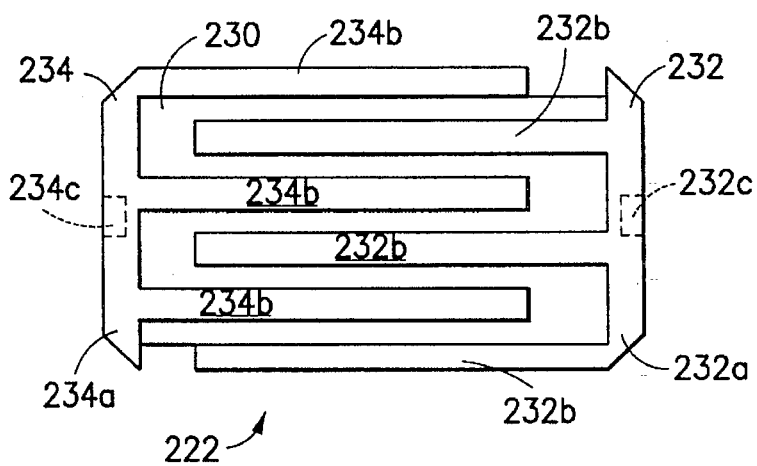
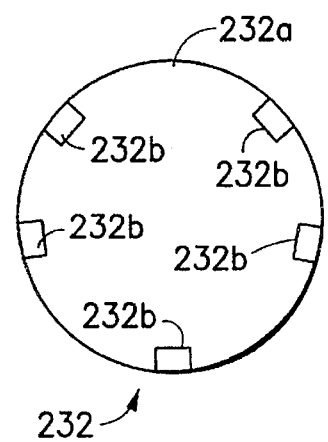
FIG. 3    FIG. 4
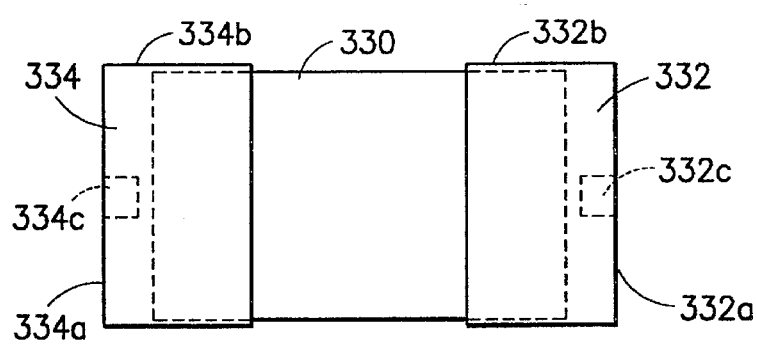
FIG. 5
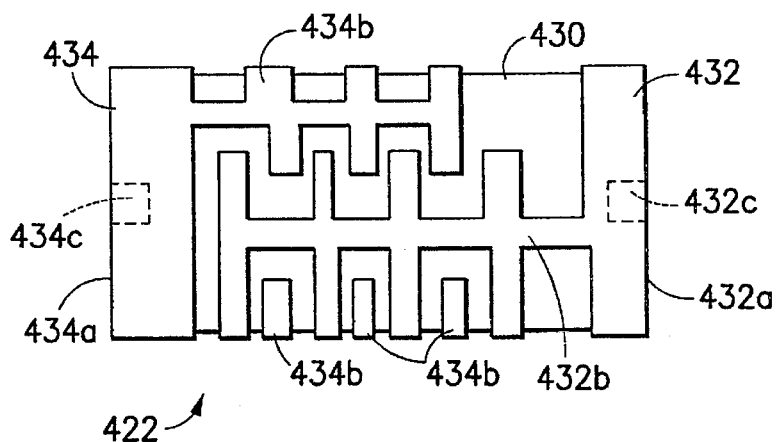
FIG. 6

BIPOLAR ROLLER ELECTRODES AND ELECTROCAUTERY PROBES FOR USE WITH A RESECTOSCOPE

This application is related to co-owned U.S. application Ser. Nos. 08/425,367, now patented U.S. Pat. No. 5,549,605 on Aug. 27, 1996 and 08/425,363 both of which were filed on Apr. 20, 1995, the complete disclosures of which are hereby incorporated herein by reference.

BACKGROUND OF THE INVENTION

1. Field of the Invention

The invention relates to endoscopic instruments. More particularly, the invention relates to electrocautery probes for use with a resectoscope or hysteroscope and specifically relates to bipolar roller electrodes used in electrocautery probes.

2. State of the Art

Electrosurgical resection is a procedure in which damaged or enlarged tissue is excised with an electrocautery probe. Transurethral resection is an electrosurgical procedure in which a portion of the prostrate is excised by means of an instrument passed through the urethra. Endometrial ablation is an electrosurgical alternative procedure to hysterectomy for women with menorrhagia (abnormal or excessive uterine bleeding). In these procedures, the instrument typically used is called a resectoscope or hysteroscope. Prior art FIG. 1 shows a typical resectoscope 10 with an electrocautery probe 12. The resectoscope 10 includes a distal tube 14 and a proximal handle 16. A telescope 18 is located in the tube 14 and is provided with a proximal eye piece 20 for viewing the interior of the bladder or other operative site. The cautery probe 12 has a distal electrode 22 which is mounted between a pair of arms 23, 25. The arms 23, 25 are joined at their proximal ends to an electrode lead 27 which is coupled via the handle 16 to a wire 24 which is coupled to a source of cautery current (not shown). A mounting sleeve 29 is provided on the probe 12 for slideably coupling it to the tube 14. The mounting sleeve 29 is typically located at the point where the arms 23, 25 are joined to the electrode lead 27. The handle 16 is generally capable of axially sliding the probe 12 and its distally mounted electrode 22 relative to the tube 14.

The ablation or resection procedure involves applying a cauterizing voltage to the electrode 22 and moving the electrode slowly over the prostate or endometrium while viewing the tissue through the scope 18. Thermal energy is applied through the electrode to the prostate or the endometrium so that tissue is excised. The resectoscope and cautery probe are also useful in other procedures for resecting the uterus, ureter, or renal pelvis.

Known electrodes for use in resectoscopes are available in many different shapes and sizes. U.S. Pat. No. 4,917,082 to Grossi et al., for example, discloses several embodiments of a "Resectoscope Electrode" including a coagulating electrode, a knife electrode, a punctate electrode, and a roller electrode, among others. Electrodes for use with resectoscopes are also widely available from Olsen Electrosurgical, Inc., Concord, Calif. They are available as blades, needles, balls, loops, spear tips, flexible wires, semi-circular wires, hooks, spatulas and blunt tips.

Recently, the generally preferred electrode for use in endometrial ablation is the roller (often referred to as "roller bar" or "roller ball") electrode. Prior art FIG. 1 shows a roller bar electrode 22. The roller bar is approximately 2.5 mm long and has a central bore 22b. It is rotatably mounted between the arms 23, 25 at the distal end of the electrocautery probe 12 by means of an axle wire 21 which extends through the central bore 22b of the electrode 22. The roller bar is supplied with a cauterizing voltage through the wire 21 which is coupled to the arms 23, 25 in the probe 12. When energized, the electrode 22 is rolled across the endometrial surface methodically until desired areas of the endometrium have been ablated. Roller bar electrodes are also used in prostatic resection.

It is generally appreciated in the art of electrocautery that bipolar cautery is safer and more effective than monopolar cautery. Monopolar electrosurgical instruments employ the instrument as one electrode, with a large electrode plate beneath and in contact with the patient serving as the second electrode. High frequency voltage spikes are passed through the instrument to the electrode of the endoscopic instrument to cause an arcing between the instrument and the proximate tissue of the patient. The current thereby generated continues through the patient to the large electrode plate beneath the patient. Monopolar cautery has the disadvantage that the current flows completely through the patient. Because control of the current path through the body is not possible, damage can occur to tissue both near and at some distance from the surgical site. In addition, it is has been observed that monopolar cautery can result in excessive tissue damage due to the arcing between the endoscopic instrument and the tissue.

In order to overcome the problems associated with monopolar cautery instruments, certain bipolar endoscopic instruments have been introduced. In bipolar electrosurgical instruments, two electrodes which are closely spaced together are utilized to contact the tissue. Typically, these bipolar instruments have two end effectors, e.g. a pair of scissor blades or a pair of forceps. One end effector acts as the first electrode, and the other end effector acts as the second electrode, with the end effectors being electrically isolated from each other and each having a separate current path back through to the handle of the instrument. Thus, in a bipolar instrument, the current flow is from one end effector electrode, through the tissue to be cauterized, to the other end effector electrode.

The use of bipolar electrodes in conjunction with resectosopes is known. U.S. Pat. No. 4,060,087 to Hiltebrandt et al. describes a simple double cutting loop electrode wherein each tungsten loop is an electrode and current flows from one loop to the other. The loops are spaced apart from each other by approximately 0.3 to 3.0 millimeters depending on the frequency of the cautery current. However, the distance between the loops must be precisely fixed to ensure cutting and avoid unintended coagulation of tissue. U.S. Pat. No. 4,116,198 to Roos discloses a similar bipolar double loop electrode as well as a bipolar electrode having a single loop and an adjacent non-loop electrode. The non-loop electrode may take the form of a coaxial cylindrical or semi-cylindrical shield or a pair of planar members mounted on opposite arms of a loop electrode. Nevertheless, there is no presently known way to utilize bipolar cautery techniques with a roller electrode used in endometrial ablation or transurethral resection.

SUMMARY OF THE INVENTION

It is therefore an object of the invention to provide a bipolar roller electrode as part of an electrocautery probe for use with a resectoscope.

It is also an object of the invention to provide a bipolar roller electrode electrocautery probe which is particularly well suited for endometrial ablation and transurethral resection.

In accord with these objects which will be discussed in detail below, a bipolar roller electrode according to the invention includes a non-conductive base having a substantially circular cross section and two electrical conductors which are placed upon the base with a gap between the conductors. The electrode is provided with a blind hole at each end thereof for rotatably mounting it between a pair of arms. Each of the two conductors preferably extends into or forms a part of a respective blind hole. An electrocautery probe according to the invention includes a pair of electrically conductive arms between which the electrode is mounted with each of the arms entering one of the blind holes in the electrode. The arms are mechanically joined together but electrically isolated from each other, and their proximal ends are individually coupled to a pair of electrode leads. A non-conductive or insulated mounting sleeve is preferably provided intermediate of the arms and the leads for slideably coupling the probe to a resectoscope. The distal end of each arm of the probe makes electrical contact with a respective one of the two conductors.

Several methods of manufacturing the electrodes are disclosed including metallizing, plating, sputtering or casting conductors on a ceramic base and selectively removing areas by etching, laser machining, conventional machining, EDM (electronic discharge machining) or ECM (electrochemical machining). Alternatively, the conductors may be formed as two caps which are machined, cast, drawn, etc. and placed over opposite ends of a ceramic base. As a further alternative, conductive paint or ink may be applied to a ceramic base using a sprayer. As still another alternative, a ceramic base may be injection molded and fired, then the conductors could be applied by casting a metal framework over the ceramic base.

According to a presently preferred embodiment of the invention, the conductors are formed with relatively complex but patterned geometries so that the conductors form an interleaved pattern on the ceramic base. This provides many locations on the electrode where current may pass from one conductor to the other. Since a large portion of the roller electrode is not in contact with tissue as it is rolled over the tissue, it is important that the conductors be arranged so that current can always pass through the tissue regardless of the position of the roller.

Additional objects and advantages of the invention will become apparent to those skilled in the art upon reference to the detailed description taken in conjunction with the provided figures.

BRIEF DESCRIPTION OF THE DRAWINGS

FIG. 3 is an enlarged side elevation view of a bipolar roller electrode according to a second embodiment of the invention;

FIG. 4 is an end view of one of the conductor caps of the electrode of FIG. 3;

FIG. 5 is an enlarged side elevation view of a third embodiment of a bipolar roller electrode according to the invention;

FIG. 6 is an enlarged side elevation view of a fourth embodiment of a bipolar roller electrode according to the invention;

DETAILED DESCRIPTION OF THE PREFERRED EMBODIMENTS

Figure 1:
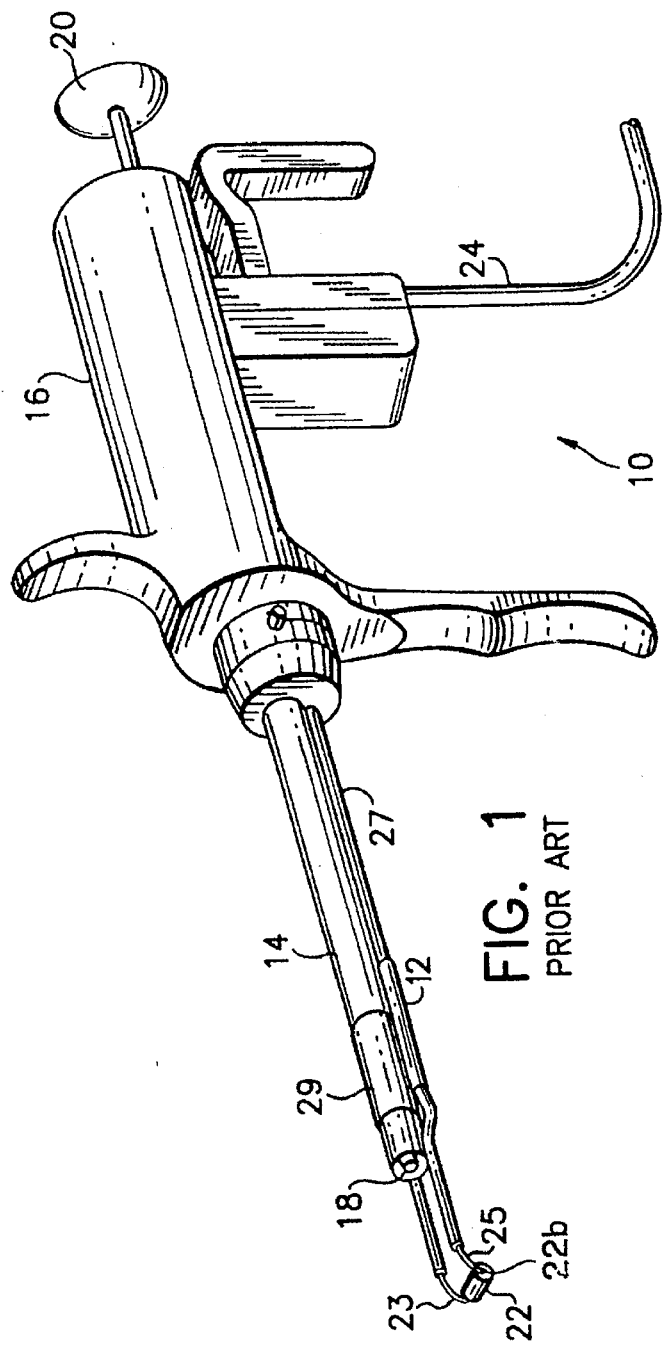
FIG. 1 is a perspective view of a prior art resectoscope having mounted thereon a prior art electrocautery probe having a monopolar roller bar electrode.
Figure 2:
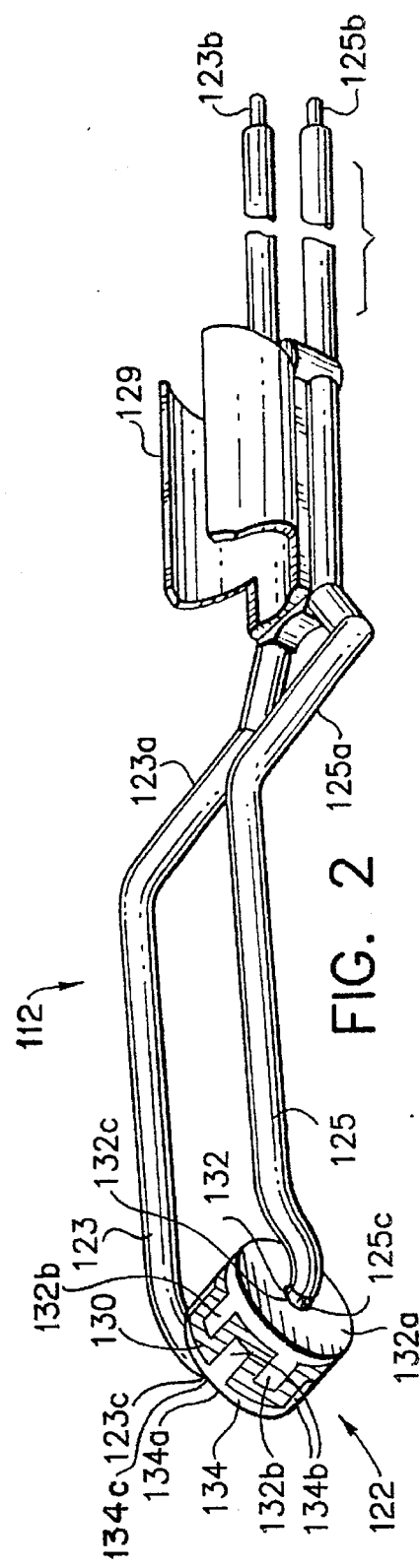
FIG. 2 is an enlarged broken perspective view of the distal end of an electrocautery probe coupled to a bipolar roller electrode according to a first embodiment of the invention.

Referring now to FIG. 2, an electrocautery probe 112 according to the invention includes an electrode 122 which is rotatably mounted between a pair of parallel arms 123, 125. The arms 123, 125 each have a conductive core and a non-conductive insulating sheath 123a, 125a. The conductive core of each arm is exposed at respective proximal ends 123b, 125b and distal ends 123c, 125c. A mounting sleeve 129 is provided near the distal ends of the arms 123, 125 for coupling the probe to a resectoscope and for maintaining the arms in a stable spaced apart position.

The electrode 122 according to a first embodiment of the invention includes a ceramic cylindrical base 130 which is shown hatched in FIG. 2. A first conductor 132 is plated onto a portion of the base 130 and a second conductor 134 is plated onto another portion of the base 130. According to a presently preferred embodiment, the base is approximately 0.175 inches long and approximately 0.12 inches in diameter and is constructed by injection molding a ceramic powder in a soft carrier and then fusing the powder in an oven. It is understood, however, that the base may be constructed of HDPE (high density polyethylene) such at ALLTEM™ or any zirconia, alumina, or titania ceramic. Alternatively, the non-conductive base may be made of a conductive material which is coated with an insulative material, such as a ceramic coated metal.

According to this first embodiment, the geometry of each conductor 132, 134 includes a plated end cap 132a, 134a and a plurality of plated longitudinal surface tines 132b, 134b. The end caps each cover substantially all of a respective flat end of the cylindrical base 130 as well as an adjacent portion of the curved surface of the cylindrical base 130. The longitudinal surface tines extend longitudinally along the curved surface from one end towards another end but stop short of reaching the other end. In addition, the surface tines are circumferentially spaced apart at regular intervals with the circumferential distance between each tine being greater than the width of each tine. The conductors may be made of copper, silver, gold, tungsten, or any other suitable material.

From the foregoing, and as illustrated in FIG. 2, it will be appreciated that the conductors 132 and 134 are plated onto the base 130 with their respective plated tines interleaved. It will also be appreciated that the plated surface tines 132b, 134b of each conductor 132, 134 are electrically coupled to the respective end caps 132a, 134a. According to the invention, each end cap 132a, 134a is provided with an axial blind hole 132c, 134c which may extend into the base 130, but which do not extend so far as to meet each other.

The electrode 122 is mounted between the distal ends 123c, 125c of the arms 123, 125 of the probe 112 by inserting the distal ends 123c, 125c into respective axial blind holes 132c, 134c. It will be appreciated that the dimensions of the holes and the non-insulated distal ends 123c, 125c should be sufficient to maintain a secure mounting of the electrode 122. It will also be appreciated that these dimensions should be sufficient to allow electrode 122 to rotate about the axis in which the axial blind holes lie and that they should be sufficient to maintain an electrical connection between respective distal ends 123c, 125c and conductor end caps 132a, 134a.

When the probe 112 is assembled as described above, it can be coupled to a resectoscope (not shown) which is capable of providing bipolar cautery current to the probe via the proximal ends 123b, 125b of the arms 123, 125. It will therefore be understood that the cautery current is conducted through the arms 123, 125 to the respective conductors 132, 134 on the electrode 122. When the current is applied during an ablation or resection procedure, the current will flow from one conductor 132 through the subject tissue to the other electrode 134. It will also be understood that, as the roller electrode is rolled over the subject tissue, at least one plated surface tine 132b, 134b from each conductor 132, 134 will contact the tissue or be in a position to pass current through the tissue.

As mentioned above, the electrode 122 according to the first embodiment of the invention is constructed of a ceramic cylindrical base which is plated with the conductors which are arranged to have end caps and interleaved longitudinal tines. FIGS. 3 and 4 show a second embodiment of an electrode 222 according to the invention where the conductors have a similar geometry, but where the electrode is assembled in a different manner.

Turning now to FIGS. 3 and 4, the second embodiment of the electrode 222 according to the invention includes a ceramic cylindrical base 230 and a pair of cast conductors 232, 234. The conductors 232, 234 are substantially identical to each other and include a frustroconical end cap portion 232a, 234a and a plurality of tines 232b, 234b. The tines are substantially orthogonal to the end cap and are arranged circumferentially relative to the end cap. Each end cap is provided with an axial bore 232c, 234c for receiving the distal ends of probe arms as described above. Depending on dimensional considerations, the bores 232c, 234c may be blind holes as described above or they may be through holes which align with blind holes in the cylindrical base 230. As with the first embodiment described above, the dimensioning and circumferential spacing of the tines is such that the tines of one conductor may be interleaved with the tines of the other conductor. The electrode 222 is assembled by press fitting the conductors 232, 234 onto respective ends of the base 230. In order to aid in the alignment of the tines, the base 230 may be provided with a plurality of surface grooves within which the tines reside when the conductors are pressed onto the base.

An alternative method of making the cast conductors is to cover the base with a pattern of wax or plastic representing the pattern of the conductors, cover the base and wax with an investment material, and to cast the conductors about the base using a lost wax or lost plastic method.

Turning now to FIG. 5, the same method of assembly as described above with reference to FIGS. 3 and 4 can be used to assemble a simpler bipolar roller electrode 322. The electrode 322 includes a ceramic cylinder base 330 and two cast or molded conductors 332, 334. The conductors 332, 334 are substantially cylindrical having an end cap 332a, 334a and a cylindrical wall 332b, 334b. The end caps are provided with bores 332c, 334c and the conductors 332, 334 are press fit onto the ends of the base 330. The electrode 322 may be preferred in certain cautery procedures where the conductors are desirably spaced relatively far apart.

As mentioned above, the conductors may be applied to the non-conductive base in several different ways and in different geometric configurations. It will be appreciated that with relatively complex geometric configurations, imprinting the base with conductive paint or ink may be the preferred way of applying the conductors. For example, FIG. 6 shows an electrode 422 according to the invention where the conductors are provided with a relatively complex geometry which makes casting or molding the conductors difficult.

Turning now to FIG. 6, the electrode 422 according to the invention includes a cylindrical non-conductive base 430 upon which conductors 432, 434 are imprinted. The imprinted conductors each include an end cap portion 432a, 434a which is imprinted on opposite flat ends of the base 430 and a branched lattice 432b, 434b which is imprinted on the curved surface of the base 430. The lattice of each conductor is arranged so that the branches of one conductor interleave with the branches of the other conductor in two dimensions. As such, it would be difficult to achieve this configuration using cast or molded conductors. Since the conductors are relatively thin 432, 434 as applied to the base 430, the base 430 is provided with blind holes 432c, 434c upon which part of the end caps 432a, 434a are imprinted. Imprinting may be achieved using an ink which contains a conductive metal powder and spraying the ink onto the base. The pattern of the conductive ink is achieved by using an ink-jet printing process or by spraying through a stencil.

It will be appreciated that the relatively complex conductor geometry described above can also be obtained by coating the entire base of the electrode with conductive material and then selectively removing the material using a number of different techniques. For example, the conductors can be deposited on the base using vapor deposition, sputtering, etc and then etched using ECM or EDM or a mechanical milling. Moreover, the coated base may be imprinted with photoresist and etched with an etchant in much the same way as a printed circuit board is made.

Figure 7:
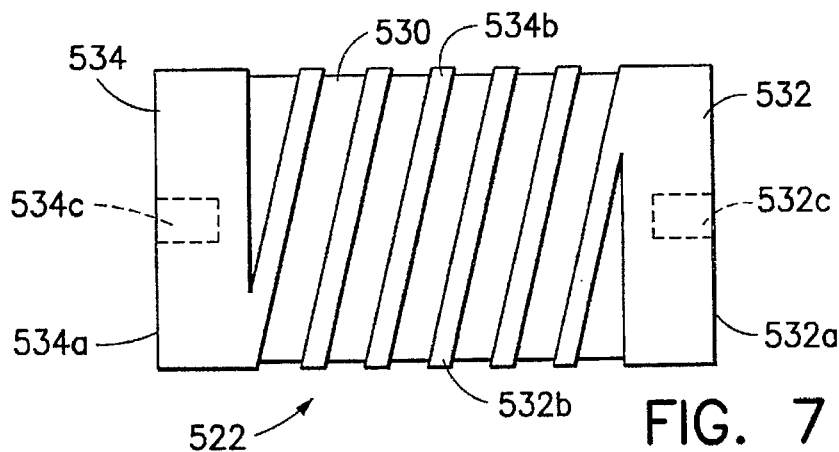
FIG. 7 is an enlarged side elevation view of a fifth embodiment of a bipolar roller electrode according to the invention.

In addition to the relatively complex conductor geometry described above, some relatively simple geometries are easier to achieve using imprinting or coating followed by milling. FIG. 7 shows an electrode 522 according to the invention which has a relatively simple conductor geometry but which is difficult to assemble using cast or molded conductors. As seen in FIG. 7, a bipolar roller electrode 522 according to the invention includes a cylindrical ceramic base 530, a first conductor 532, and a second conductor 534. Each of the conductors has an end cap portion 532a, 534a which substantially covers a respective flat end of the base 530 and a spiral thread 532b, 534b which wraps around a portion of the curved surface of the base 530. The two conductors are substantially identical so that their spiral threads interleave as shown in FIG. 7. While the geometry of the spiral threads is not complex, it is easier to apply this conductor to the base using the imprinting or coating followed by milling techniques because of the way the spiral threads interleave. The electrode 522 is provided with blind hole bores 532c, 534c in opposite flat ends for rotational mounting and electrical coupling as described above.

Figure 8:
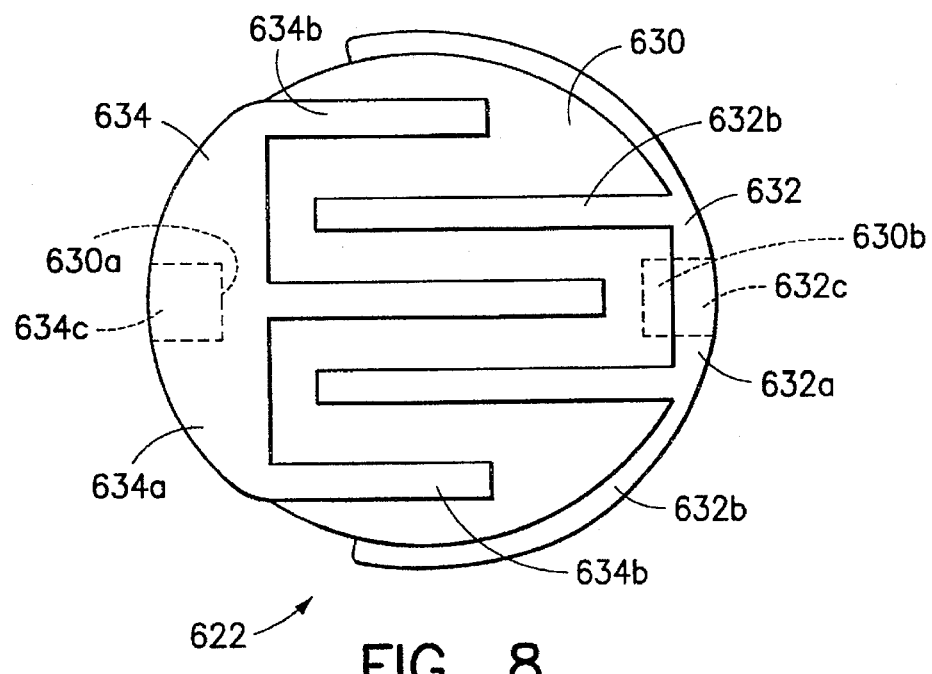
FIG. 8 is an enlarged side elevation view of a sixth embodiment of a bipolar roller electrode according to the invention.
Figure 9:
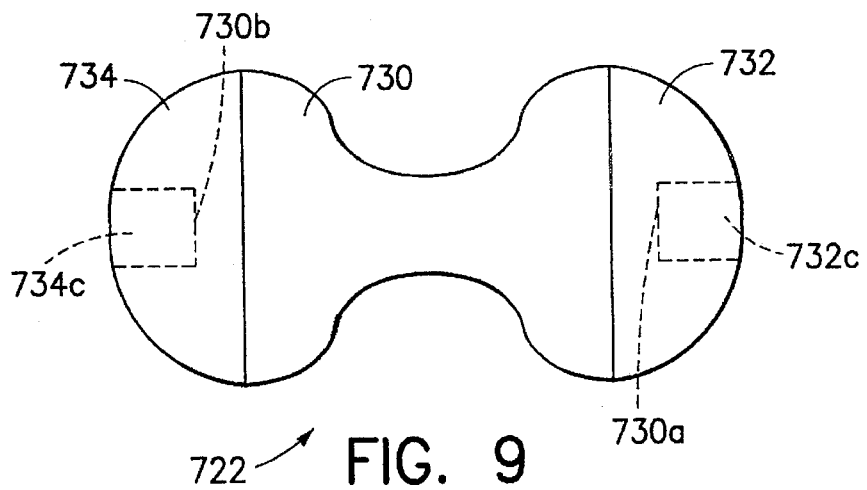
FIG. 9 is an enlarged side elevation view of a seventh embodiment of a bipolar roller electrode according to the invention.

Thus far, the embodiments of the bipolar roller electrode according to the invention have included a substantially cylindrical base upon which a pair of conductors are placed. However, it is not an essential element of the invention that the non-conductive base be cylindrical. FIGS. 8 and 9 show electrodes according to the invention having non-cylindrical base members.

The bipolar electrode 622 of FIG. 8 includes a substantially spherical non-conductive base 630 and two conductors 632, 634. The base 630 is provided with a pair of axial polar blind hole bores 630a, 630b. Each conductor has a polar cap portion 632a, 634a and a plurality of longitudinal tines 632b, 634b. Each of the polar cap portions 632a, 634a has an axial throughbore 632c, 634c which aligns with a respective blind hole bore 630a, 630b in the base 630. The electrode 622 may be assembled using any of the methods described above and is coupled to the probe of FIG. 2 in the same way as the other electrodes described herein. It will be appreciated that the bipolar roller ball electrode 622 may be made with conductors having various geometries such as those described above.

In addition to cylindrical and spherical electrodes, the bipolar roller electrodes according to the invention may be made in any shape which is symmetrical about an axis and has a substantially circular cross section. For example, as shown in FIG. 9, an electrode 722 according to the invention has a non-conductive base 730 which is shaped as a "dumb bell" and two end cap conductors 732, 734. The conductors each have an axial hole 732c, 734c aligned with an axial blind hole 730a, 730b in the base 730. The electrode 722 may be assembled using any of the methods described above and is coupled to the probe of FIG. 2 in the same way as the other electrodes described herein. It will be appreciated that the electrode 722 may be made with conductors having various geometries such as those described above.

Figure 10:
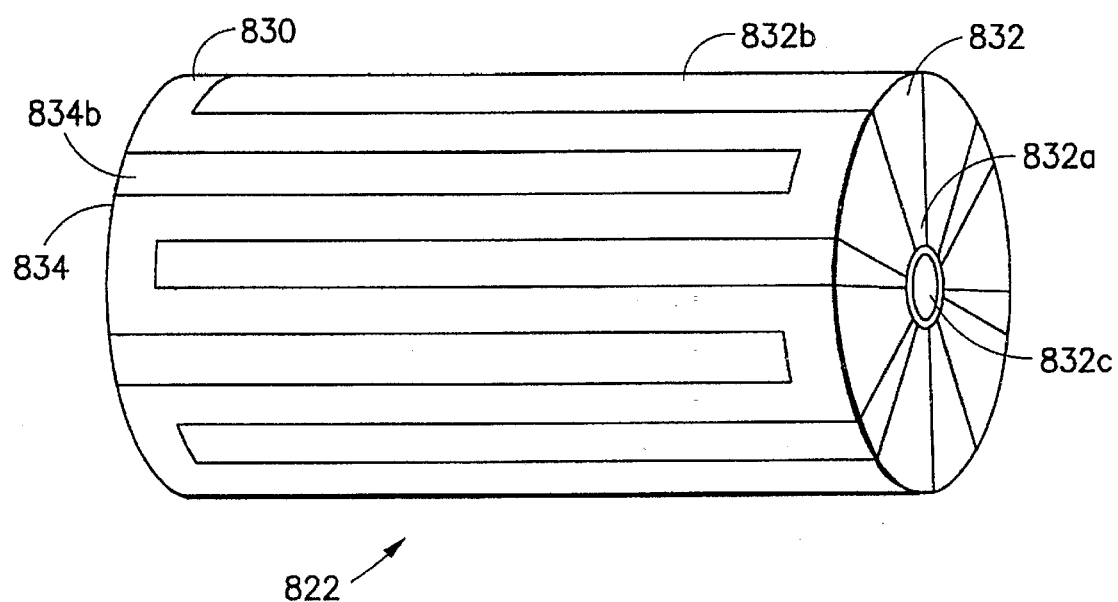
FIG. 10 is an enlarged perspective view of an eighth embodiment of a bipolar roller electrode according to the invention.

As mentioned above, the conductors of the electrode make electrical contact with the distal ends of the respective arms of the cautery probe. Thus far, the electrodes described above have been shown with end caps which cover substantially all of the respective ends of the nonconductive base of the electrode. It will be understood by those skilled in the art, however, that it is not necessary for the end portions of the conductors to cover all of the respective ends of the base in order to make contact with a respective arm of the cautery probe. Thus, as seen in FIG. 10, an electrode 822 according to the invention resembles the electrode 122 described above having a non-conductive base 830 and a pair of conductors 832, 834 plated thereon. In this embodiment, each conductor has end portions, e.g., 832a, which are configured as traces from surface tines, e.g., 832b to a respective blind hole, e.g., 832c. While FIG. 10 shows the traces as radial traces to the longitudinal tines, it will be understood that other configurations could also be used.

There have been described and illustrated herein several embodiments of a bipolar roller electrode for use with an electrocautery probe in a resectoscope. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other dimensions and materials could be utilized. Also, while conductors having various interleaved geometries have been disclosed, it will be recognized that other interleaved geometries could be used with similar results obtained. Moreover, while particular configurations have been disclosed in reference to features of the electrocautery probe carrying the electrode, it will be appreciated that other configurations of a cautery probe could be used with the provided electrodes. Furthermore, while the probes and electrodes have been disclosed as having particular utility in conjunction with a resectoscope, it will be understood that the cautery probes and electrodes disclosed herein can be used in other surgical procedures without requiring a resectoscope. It will therefore be appreciated by those skilled in the art that yet other modifications could be made to the provided invention without deviating from its spirit and scope as so claimed.

We claim:

1. A bipolar roller electrode for use in an electrocautery probe having two arms between which said electrode is mounted for rotation, said electrode comprising:
    a) a non-conductive base member having a substantially circular cross section, a first end, a second end, and a surface between said first and second ends, said first and second ends defining an axis of rotation therebetween;
    b) a first conductor having a first end portion covering at least part of said first end of said base member and a first surface portion covering a portion of said surface of said base member;
    c) a second conductor having a second end portion covering at least part of said second end of said base member and a second surface portion covering a portion of said surface of said base member, wherein
    said first surface portion is interleaved with said second surface portion, and
    said first end portion has means for electrically coupling to one of the two arms and said second end portion has means for electrically coupling to the other of the two arms such that said roller electrode is rotatable about said axis of rotation between said two arms.

2. A bipolar roller electrode according to claim 1, wherein:
    said first surface portion includes a first plurality of tines and said second surface portion includes a second plurality of tines.

3. A bipolar roller electrode according to claim 1, wherein:
    said first surface portion includes a first lattice and said second surface portion includes a second lattice, wherein said first lattice and said second lattice are interleaved in two dimensions.

4. A bipolar roller electrode according to claim 1, wherein:
    said first surface portion includes a first spiral thread and said second surface portion includes a second spiral thread.

5. A bipolar roller electrode according to claim 1, wherein:
    said base member is substantially cylindrical.

6. A bipolar roller electrode according to claim 1, wherein:
    said base member is substantially spherical.

7. A bipolar roller electrode according to claim 1, wherein:
    said surface of said base member is at least partially concave.

8. A bipolar roller electrode according to claim 1, wherein:
    said surface of said base member is at least partially convex.

9. A bipolar electrocautery probe for use in a resectoscope, comprising:
    a) a pair of conductive arms having proximal and distal ends, said arms being mechanically joined to each other at a point proximal of their distal ends and electrically isolated from each other;
    b) a pair of electrode leads coupled to said proximal ends of said conductive arms and extending proximally therefrom; and c) a roller electrode rotatably mounted between said distal ends of said conductive arms, said roller electrode comprising,
   (i) a non-conductive base member having a substantially circular cross section, a first end, a second end, and a surface between said first and second ends, said first and second ends defining an axis of rotation therebetween,
   (ii) a first conductor having a first end portion covering at least part of said first end of said base member and a first surface portion covering a portion of said surface of said base member,
   (iii) a second conductor having a second end portion covering at least part of said second end of said base member and a second surface portion covering a portion of said surface of said base member, wherein said first conductor makes electrical contact with a first one of said pair of conductive arms and said second conductor makes electrical contact with a second one of said pair of conductive arms such that said roller electrode is rotatable about said axis of rotation between said two arms.

* * * * *